United States Patent
Picco et al.

(10) Patent No.: US 11,190,357 B2
(45) Date of Patent: Nov. 30, 2021

(54) FRAMEWORK FOR ENSURING SOFTWARE COMPONENTS ARE NOT CORRUPTED

(71) Applicant: Revive Solutions, Inc., San Mateo, CA (US)

(72) Inventors: David Picco, San Marcos, CA (US); Gaurav Rao, Halifax (CA)

(73) Assignee: Avive Solutions, Inc., San Francisco, CA (US)

(*) Notice: Subject to any disclaimer, the term of this patent is extended or adjusted under 35 U.S.C. 154(b) by 269 days.

(21) Appl. No.: 16/402,516

(22) Filed: May 3, 2019

(65) Prior Publication Data
US 2019/0356492 A1 Nov. 21, 2019

Related U.S. Application Data

(60) Provisional application No. 62/673,345, filed on May 18, 2018.

(51) Int. Cl.
| | |
|---|---|
| *H04L 9/32* | (2006.01) |
| *H04L 29/08* | (2006.01) |
| *G06F 21/51* | (2013.01) |
| *H04L 29/06* | (2006.01) |
| *G06F 21/64* | (2013.01) |
| *A61N 1/04* | (2006.01) |

(52) U.S. Cl.
CPC ............ *H04L 9/3236* (2013.01); *G06F 21/51* (2013.01); *G06F 21/64* (2013.01); *H04L 67/125* (2013.01); *H04L 69/22* (2013.01); *A61N 1/046* (2013.01)

(58) Field of Classification Search
None
See application file for complete search history.

(56) References Cited

U.S. PATENT DOCUMENTS

| | | | | |
|---|---|---|---|---|
| 5,892,904 | A | * 4/1999 | Atkinson | G06F 21/51 726/22 |
| 5,996,073 | A | * 11/1999 | Lee | G06F 11/3013 713/1 |
| 6,334,070 | B1 | * 12/2001 | Nova | A61N 1/3993 607/5 |
| 6,535,894 | B1 | * 3/2003 | Schmidt | G06F 8/658 |

(Continued)

OTHER PUBLICATIONS

No stated author; Linux Standard Base Core Specification 3.1; 2005; retrieved from the Internet https://refspecs.linuxbase.org/LSB_3.1.1/LSB-Core-generic/LSB-Core-generic/book1.html; pp. 1-24, as printed. (Year: 2005).*

(Continued)

*Primary Examiner* — Michael W Chao
(74) *Attorney, Agent, or Firm* — Beyer Law Group LLP

(57) ABSTRACT

A variety of frameworks, methods and container structures are described that are well suited for use in conjunction with medical devices and/or medical device support applications that are configured to be used in conjunction with a medical device. The described arrangements are well suited for use by applications executed on external devices such as a mobile communication device or an interface unit that are distinct from the medical device that the external device is being used in conjunction with. One specific application relates to defibrillator support applications executing on devices that are arranged to work in conjunction with a defibrillator, such as an automated external defibrillator.

25 Claims, 7 Drawing Sheets

(56) References Cited

U.S. PATENT DOCUMENTS

| | | | | |
|---|---|---|---|---|
| 7,478,142 B1* | 1/2009 | Veditz | G06F 9/445 | 709/218 |
| 7,577,848 B2* | 8/2009 | Schwartz | G06F 21/52 | 711/216 |
| 7,685,596 B1* | 3/2010 | Webb | G06F 16/13 | 717/177 |
| 9,383,984 B2* | 7/2016 | Mantripragada | G06F 8/61 | |
| 10,277,396 B2* | 4/2019 | Ramos | H04L 9/0637 | |
| 2002/0059561 A1* | 5/2002 | Foster | G06F 11/3688 | 717/126 |
| 2003/0167407 A1* | 9/2003 | Howard | H04L 69/22 | 713/191 |
| 2005/0049790 A1* | 3/2005 | Holman | G06F 8/61 | 702/3 |
| 2005/0240795 A1* | 10/2005 | Paller | H04L 43/0805 | 714/1 |
| 2007/0101197 A1* | 5/2007 | Moore | G06F 8/61 | 714/38.1 |
| 2007/0234343 A1* | 10/2007 | Gouge | G06F 21/51 | 717/174 |
| 2008/0163383 A1* | 7/2008 | Kumar | G06F 21/57 | 726/29 |
| 2008/0201705 A1* | 8/2008 | Wookey | G06F 8/658 | 717/175 |
| 2009/0172640 A1* | 7/2009 | Geismar | G16H 40/40 | 717/121 |
| 2010/0062844 A1* | 3/2010 | Crowder, Jr. | G07F 17/32 | 463/29 |
| 2011/0010543 A1* | 1/2011 | Schmidt | H04L 63/123 | 713/168 |
| 2011/0265164 A1* | 10/2011 | Lucovsky | G06F 8/61 | 726/7 |
| 2012/0090025 A1* | 4/2012 | Milner | G06F 21/564 | 726/22 |
| 2012/0102485 A1* | 4/2012 | Goldman | G06F 8/64 | 717/176 |
| 2012/0154128 A1* | 6/2012 | Cho | G05B 15/02 | 340/12.5 |
| 2012/0240125 A1* | 9/2012 | Danko | G06F 9/50 | 718/104 |
| 2012/0296397 A1* | 11/2012 | Vansickle | A61N 1/3605 | 607/59 |
| 2013/0275596 A1* | 10/2013 | Subramaniam | H04L 41/04 | 709/226 |
| 2016/0232010 A1* | 8/2016 | Dicks | G06F 8/654 | |
| 2016/0366112 A1* | 12/2016 | Gropper | H04L 63/0823 | |
| 2017/0206071 A1* | 7/2017 | Kirkpatrick | G06F 9/44521 | |
| 2018/0168463 A1* | 6/2018 | Morris | A61B 5/4836 | |
| 2018/0300220 A1* | 10/2018 | Agarwal | G06F 11/3612 | |
| 2018/0300499 A1* | 10/2018 | Agarwal | G06F 21/6245 | |
| 2019/0205112 A1* | 7/2019 | Salameh | G06F 8/65 | |

OTHER PUBLICATIONS

No stated author; Jarsigner, Oracle Java SE Documentation; Mar. 2018; retrieved from the Internet https://docs.oracle.com/javase/7/docs/technotes/tools/windows/jarsigner.html; pp. 1-13, as printed. (Year: 2018).*

Fernandez-Sanguino; Securing Debian Manual 3.19; 2017; retrieved from the Internet https://www.debian.org/doc/manuals/securing-debian-manual/; pp. 1-14, as printed. (Year: 2017).*

* cited by examiner

FRAMEWORK FOR ENSURING SOFTWARE COMPONENTS ARE NOT CORRUPTED

CROSS-REFERENCE TO RELATED APPLICATIONS

The present application claims the priority of U.S. Provisional Patent Application No. 62/673,345 filed May 18, 2018, which is incorporated herein by reference in its entirety.

FIELD

The present disclosure relates generally to frameworks, methods and container structures for ensuring that software components used in conjunction with medical devices are not corrupted. The described approaches are particular useful in circumstances in which an application having a lower security level uses components requiring higher security levels.

BACKGROUND

There are a number of circumstances where it is desirable to validate software components that are used in medical devices or in separate devices that are used in conjunction with medical devices. One such example is when a mobile communication device, a personal computer or other interface device that is not regulated, or less rigorously regulated, is used in connection with a regulated medical device. That is medical devices that are regulated by governmental agencies such as the U.S. Food and Drug Administration (FDA), the European Medicines Agency (EMA) and/or corresponding regulatory bodies in other jurisdictions. In such circumstances it is important to be able to guarantee that deliverable software components such as audio or video files, screen images, algorithms etc. that are provided for use by the unregulated device are valid and not corrupted. It is also desirable to deliver such components in a way that provides easy access to properties of the delivered components such as version information and other properties that may be desirable to log in log files to ensure regulatory compliance if and when the components are used.

Of course, there are a variety of other applications where it is desirable to be able to validate and/or identify properties of software components delivered to a medical device or to devices used in conjunction with a medical device. The present disclosure describes frameworks, methods and container structures that are well suited for ensuring that software components used in conjunction with medical devices are not corrupted.

SUMMARY

A variety of frameworks, methods and container structures are described that are well suited for use in conjunction with medical devices and/or medical device support applications that are configured to be used in conjunction with a medical device. The described arrangements are well suited for use by applications executed on external devices such as a mobile communication device or an interface unit that are distinct from the medical device that the external device is being used in conjunction with. One specific application relates to defibrillator support applications executing on devices that are arranged to work in conjunction with a defibrillator, such as an automated external defibrillator.

In one aspect, a method for validating of a container file is described. The container file includes a container header and one or more assets suitable for use by the medical device support application. Each asset including an asset header and asset data. At least a portion of the container file is hashed using a first hashing protocol (which is optionally a cryptographic hash) to create a first hash value. The hashed portion of the container file includes at least all of the assets. The first hash value is compared to a container file hash stored in the container header to determine whether the first hash value matches the container file hash. If the first hash value and the container file hash do not match, the container file is treated as not valid.

Each asset in the container file is also individually hashed using a hashing protocol that may be the same as, or different than the hashing protocol used to hash the container file. The hashed portion of the asset includes at least the asset data (sometimes referred to as the body of the asset). The resulting asset validation hash value is compared to an original asset hash value stored in the asset header. If the asset validation hash value and the original asset hash value do not match, the container file is treated as not valid. With the described approach, the container file is only validated when at least the first hash value matches the container file hash value and each asset validation hash value matches the associated original asset hash value.

In some embodiments, the application program that utilizes the container file includes a required assets list. When a required assets list exists, the validation can also verify that all assets identified in the required assets list are present in the container file. If one or more assets identified in the required assets list are not present in the container file, the container file is treated as not valid.

In some embodiments, the medical device is an automated external defibrillator or other defibrillator and the medical device support application is a defibrillator support application.

In some embodiments, the support application is installed and executes on an external device that is separate from the defibrillator (or other medical device). In some embodiments, user instructions for the medical device are displayed on a screen on the external device using one or more of the assets from the validated container file. In some embodiments, a message is displayed on the display screen informing the user to follow instructions from the defibrillator in certain circumstances when the container file is not valid.

In some embodiments, the validation is performed by the support application when the container file is initially received by the support application. In some embodiments, the validation is performed each time the support application is launched. In some embodiments, each asset is validated again immediately before it is used.

In another aspect some specific container file structures are described. In some specific implementations, each asset header includes (i) an asset file size field having a file size indicator that indicates a size of the associated asset, (ii) an asset hash field that includes an asset hash that is a hash of at least the asset data for the associated asset, and (iii) a path field that identifies at least a portion of a path suitable for accessing the asset. In some specific implementations, the container header includes (i) a file format version field that includes a file format version indicator, (ii) a container size field that includes a container size indictor that indicates a size of the container, (iii) a container file hash field that includes a container file hash that is a hash of at least the plurality of assets including the asset header and asset data associated with each asset. The container file hash is a hash of at least the container header and the plurality of assets including the asset header and asset data associated with each asset.

In some embodiments, the assets contained in the asset file include a multiplicity of components for use in instructions generated by the medical device support application to help guide an operator's use of the medical device.

In some embodiments, the container file hash and the asset hashes and are cryptographic hashes. In some embodiments, the path is a relative path.

In some embodiments, each asset header further includes at least one of an asset header size field having an asset header size indicator that indicates a size of the asset header, and a path size field that includes a path size indicator that indicates a size of the path field. In some embodiments, the container header further includes one or more of (i) a number of assets field that includes a number of assets identifier that indicates the number of assets contained in the container file; (ii) a creation time field that includes a creation time indicator that identifies a file creation date and time; (iii) a file description field that includes a description of the file; and (iv) a file description size indicator that indicates a size of the description of the file.

In another aspect, methods of creating such a container file are described.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

Figure 1:
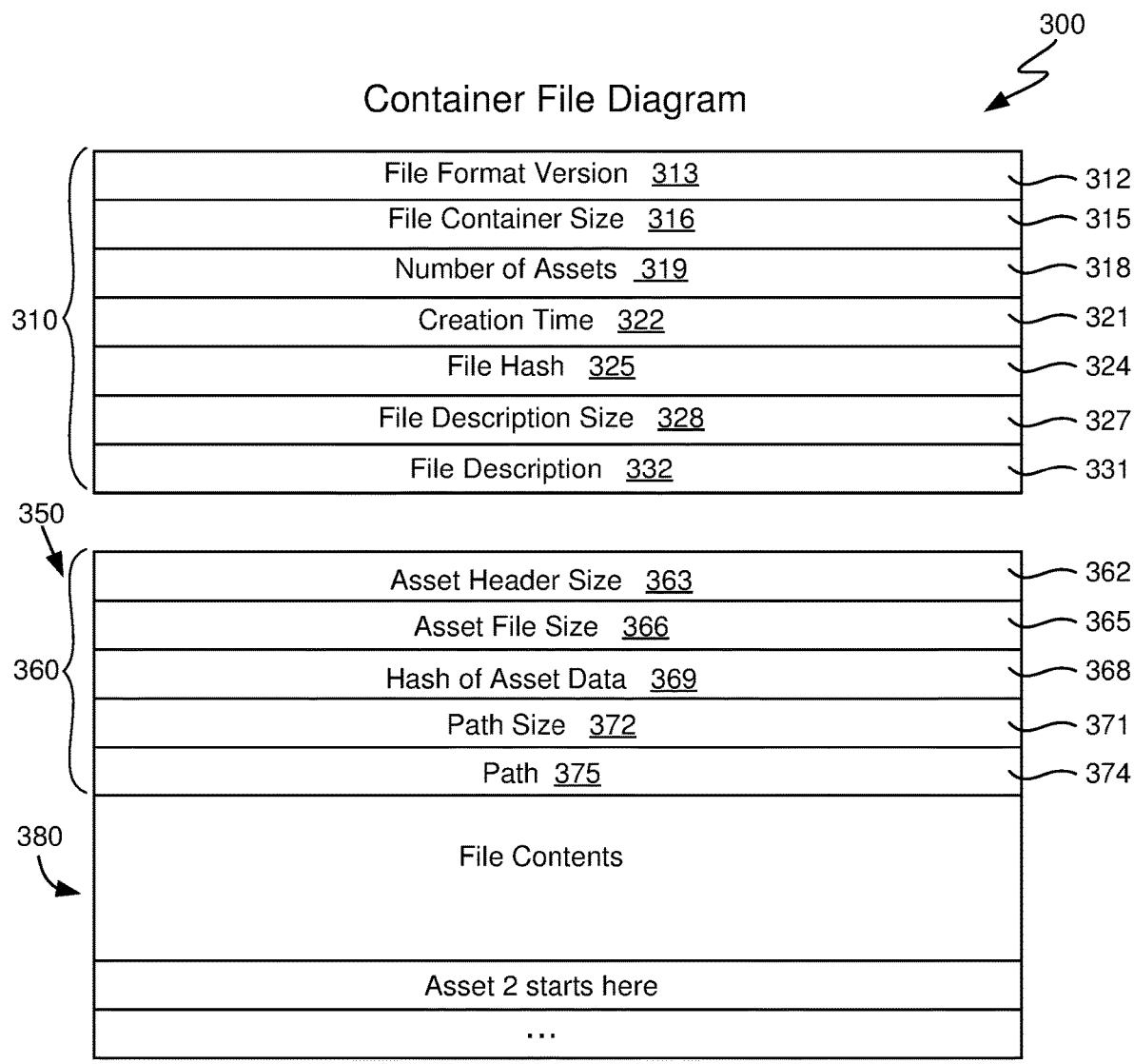
FIG. 1 is a file diagram showing the structure of a representative container file in accordance with a first embodiment.

The present disclosure relates generally to frameworks, methods and container structures for ensuring that software components used in conjunction with medical devices are valid and not corrupted. The described approaches may be used in a variety of different circumstances and are particularly useful in circumstances in which a software component requiring a relatively higher security/integrity level may be used by an application having a relatively lower security/integrity level. An example of that may be a non regulated or lower class regulated software application such as a smartphone app is used in conjunction with a regulated or higher regulated medical device and provides operating instructions for such medical device.

The Applicant is developing defibrillators that may include a number of connectivity features and/or are well suited for use in conjunction with mobile phones and/or interface devices that are separate from the defibrillator. By way of example, U.S. Pat. Nos. 10,029,109, 10,112,054, and 10,071,256 and U.S. application Ser. Nos. 16/145,657; 16/146,096 and 16/146,743 (each of which is incorporated herein by reference) describe a few such devices. Therefore, the inventions will be described primarily in the context of defibrillators. However, it should be appreciated that the described approaches can be used to ensure that software components are not corrupted in a wide variety of other medical device applications.

Some of the described systems contemplate that an external device such as a mobile phone or an independent interface device may sometimes be used in conjunction with the defibrillator during emergency uses of the defibrillator. In some circumstances, the external device displays user instructions that correspond to and complement auditory instructions provided by the defibrillator during emergency use of the defibrillator. For example, when an AED instructs a user to adhere a defibrillation electrode pad to a patient's chest, the cell phone or interface device may display a corresponding or complementary graphic instruction composed of one or more images, cine-loops, video segments and/or textual materials that show and/or describe the proper placement of the electrode pad(s). Other complimentary graphic instructions can be provided that correspond to other specific use instructions. U.S. patent application Ser. No. 16/145,657 and 62/787,872, each of which is incorporated herein by reference, provide examples of such systems.

Each of the graphic user instructions displayed on the external device has one or more corresponding software components or objects (sometimes referred to herein as "assets") that are used by the external device to render the desired content. These assets may include files that contain the images, text, graphics, video segments, pictures, cine-loops, audio files, etc. that a processor on the external device uses to render the desired user instruction. For safety purposes, it is important to ensure that any such software components utilized by the external device are valid and uncorrupted. This is particularly important because the manufacturer of the defibrillator (or other medical device) who would typically create the software application used to render the instructions often will not have control over the device (such as a personal cell phone) that is being used to render the instructions.

In general, the manufacturer of the medical device may have a number of software components/asset that it wishes to regulate. The desire to regulate the use of specific software components may be inspired by internal security guidelines, and/or by external influences or guidelines such as the need to show control of software components whose use may be regulated by a government agency such as the U.S. Food and Drug Administration (FDA). In one proposed embodiment that will be described with reference to FIG. 1, all of the regulated components are built into a single container file 300. The container file is constructed with security in mind so that the presence and integrity of the components contained therein can be verified before the components are used.

In the first described approach, each component (asset) is hashed before it is inserted into the container file and the hash is included in the component (asset) header. When all of the components have been inserted into the container file, the populated container file itself is hashed and the container file hash is inserted into a container file header. The resulting container file is a single file that contains all (one or more) of the regulated components. This container file can be copied and distributed to other systems because it contains multiple hashes to ensure file integrity. The container file hash can be used to ensure that all intended components are present and that nothing extraneous has been added to corrupt the container file. Furthermore, each component has its own hash that can be used to verify that the component itself has not been altered in any way.

FIG. 1 is a file diagram showing the structure of a representative container file. The container file 300 includes a container header 310 and one or more assets 350. Each asset 350 contains an asset header 360 and the asset contents 380 (e.g., the asset file) which is sometimes referred to as the body of the asset. A container file 300 may include any number of assets. By way of example, in various applications, the container file may contain a few, tens, hundreds, or thousands of assets.

The container header 310 includes a number of fields. However, it should be appreciated that the specific fields included in the container header, as well as the format of their respective contents, may vary in accordance with the needs of any particular implementation. In the illustrated embodiment, the container header 310 includes File Format Version field 312, File Container Size field 315, Number of Assets field 318, Creation Time field 321, File Hash field 324, File Description Size field 327 and File Description field 331.

The File Format Version field 312 stores a File Format Version indicator 313 that indicates the file format version used in the container file. This version number may be read by any program that reads the container file so that the program knows how to interpret/decompile the container file 300.

The File Container Size field 315 stores a File Container Size indicator 316 that indicates the size of the container. The container size can be indicated in any suitable format.

Number of Assets field 318 contains a Number of Assets indicator 319 that identifies the number of distinct assets that are stored within the container file 300. As suggested above, the number of assets included in the file, as well as their respective sizes can vary widely—from one or a few to thousands or more. In the example above where the medical device is an AED and the container file contains user instructions intended for display during emergency of the defibrillator, there may be tens of different instructions. Each user instruction will have at least one, and often multiple different associated assets. The assets associated with any particular instruction may include one or more images, videos, animations, cine-loops, text strings, icons, audio files, etc. For example, a particular instruction may have several associated assets including an image displayed at a top portion of the graphic frame associated with the instruction, a short animation displayed near the bottom of the frame, one or more text boxes and optionally an audio file. Other instructions may have more, fewer or different associated assets. Furthermore, when the AED has a pediatric mode that utilizes different graphics and/or different instruction for pediatric patients than adult patients, there may be another set of assets for use when the AED is in the pediatric mode. Similarly, if the AED has multiple language capabilities (e.g., English/Spanish, French/German/English, Mandarin/Cantonese, etc.) there may be additional sets of assets for use when the AED is being used in different language modes.

In addition to components intended for use during emergency use of the AED, it may be desirable to include components associated with non-emergency uses of the AED in the container file. These might include components used in association with training, monitoring, and/or maintenance of the AED. Thus, it should be appreciated that the container file 300 can sometimes include a large number of assets.

Creation Time field 321 contains a Creation Time indicator 322 that indicates the time and date that the file was created. The creation time can be stored in any suitable format.

File Hash field 324 contains a hash 325 of the container file. This hash value may be used to validate the container file. That is, a software program that desires to use the container file 300 can hash the container file using the appropriate hashing algorithm and compare the resulting hash value to the hash value stored in File Hash field 324. If the hash values match, the container file is validated. If not, the container file may be treated as corrupted and handled accordingly. This could include discarding or otherwise not using the container file, performing any desired logging, requesting a new container file, etc.

A cryptographic hashing algorithm may optionally be used to create the stored hash value so that the stored hash is a cryptographic hash. The same cryptographic hashing algorithm would then be used by the reading program to create a validation hash that is used to validate the container file. Any of a variety of publically available cryptographic hashing algorithms may be utilized to hash the container file to thereby create the stored and validation hash values.

There is some flexibility in defining the portions of the container file that are hashed to create the container hash 325. Preferably the components of container file 300 that are hashed to create the hash 325 include all of the assets 350 including both the asset headers 360 and the asset bodies 380. In some embodiments, some or all, of the container header 310 itself is also included in the materials that are hashed to create the hash 325. When the entire container header 310 is included in the materials that are hashed, known techniques can be used to insert the hash value into the header after the hashing algorithm has been executed.

File Description field 331 contains a description 332 of the container file. In some implementations the file description is implemented as a variable length text string. When the description is allowed to have a variable length, the file container may also include a File Description Size field 327 that stores a File Description Size indicator 328 that indicates the size of the file description 332.

Although a number of specific container header fields have been described herein, it should be appreciated that additional fields can be added, selected fields can be eliminated or changed and the orders of the various fields may be varied in other embodiments.

The container file 300 also has a set of assets 350 with each asset including an asset header 360 and a body (contents) 380. The asset headers 360 include a number of fields and the specific fields included in the asset header, as well as the format of their respective contents, may vary in accordance with the needs of any particular implementation. In the illustrated embodiment, the asset header 360 includes an Asset Header Size field 362, Asset File Size field 365, an Asset Hash field 368, a Path Size field 371, and a Path field 374.

Asset Header Size field 362 stores an Asset Header Size indicator 363 that indicates the size of the asset header.

Asset File Size field 365 stores a File Size indicator 366 that indicates the size of the asset contents body 380 although it should be appreciated that in other embodiments, the File size indicator can be arranged to indicate the combined size of the asset header and asset body.

Asset Hash field 368 contains a hash 369 of the asset. This hash value may be used to validate the asset. That is, a software program that desires to use the asset 350 can hash the asset using the appropriate hashing algorithm and compare the resulting asset hash value to the asset hash value stored in Asset Hash field 368. If the hash values match, the asset is validated. If not, the asset may be treated as corrupted and handled accordingly. This could include discarding or not using the corrupted asset, discarding or not using the entire container file, performing any desired logging, requesting a new container file, etc.

Like the container hash, a cryptographic hashing algorithm may optionally be used to create the stored asset hash value so that the stored asset hash is a cryptographic hash. The hashing algorithm (cryptographic or otherwise) may be the same or different than the hashing algorithm used to hash the container file.

Also like the container hash, there is some flexibility in defining the portions of the asset that are hashed to create the asset hash 325. For example, the asset body 380 alone may be hashed, or a combination of the header (or a portion thereof) and the asset body may be hashed. It is noted that the container hash preferably hashes the full assets (including the asset headers) and therefore has the effect of hashing the asset hashes, which can further improve security.

Path field 374 stores the relative path 375 (including the file name) for the asset. The path 375 is provided so that the consuming application can determine the location of the asset in the context of the device/application file system. In some embodiments the path is stored as a variable length text string. In such embodiments, a Path Size field 371 may be provided to hold a Path Size indicator 372 that indicates the size of the asset contents/body 380.

Figure 2:
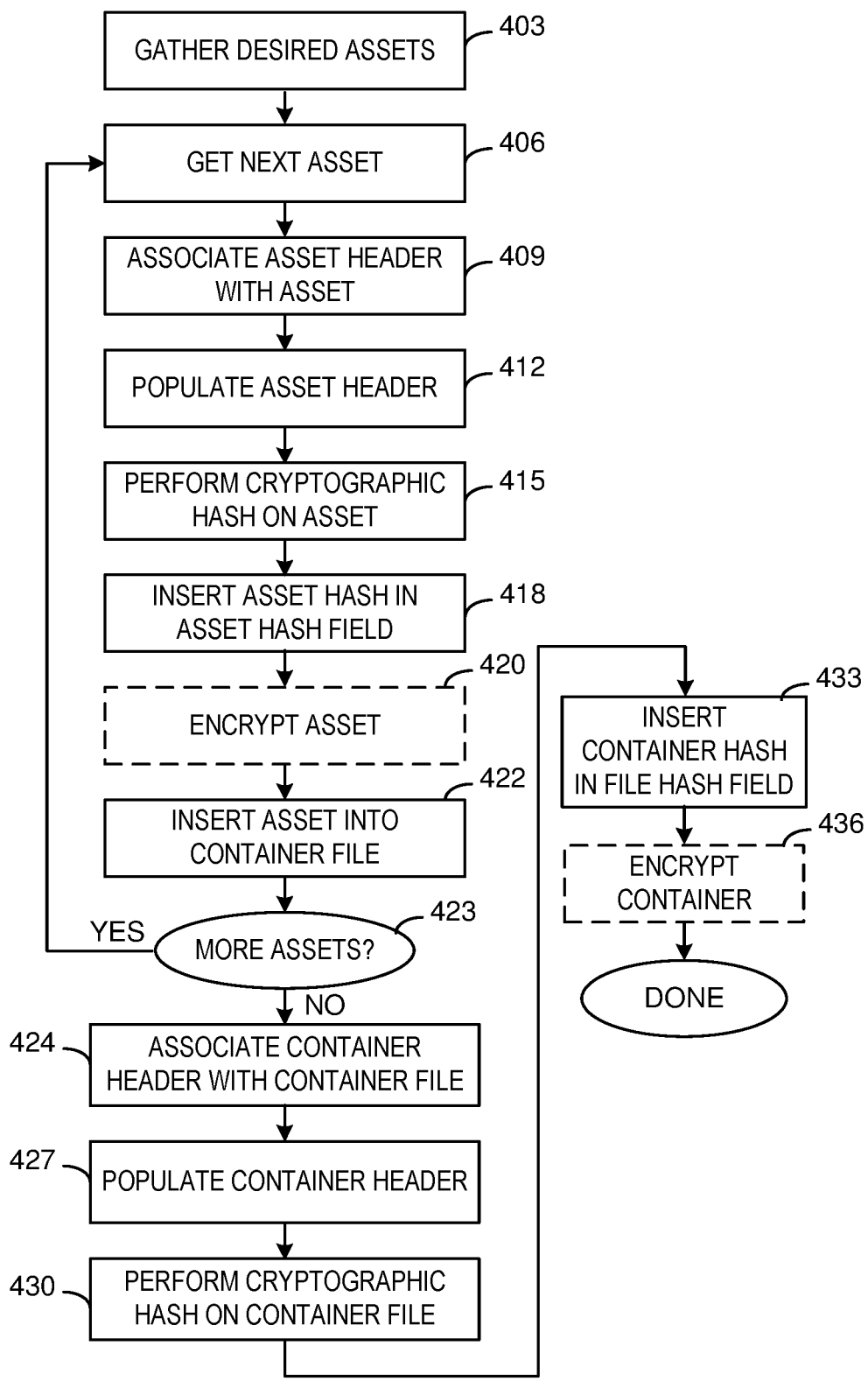
FIG. 2 is a flow chart illustrating a representative method of creating the container file of FIG. 1.

Referring next to FIG. 2, a method of creating the container file 300 will be described. FIG. 2 is a flow chart that illustrates a number of steps that may be followed to create a suitable container file. However, it should be appreciated that the flow chart is provided primarily to facilitate a description of the creation of a container file and that the order of the steps may varied in any particular application and that in various embodiments selected steps may be combined, parsed into multiple components, eliminated, revised and/or performed in other ways.

In the illustrated embodiment, the assets that are intended for inclusion in the container are initially gathered as represented by block 403. As suggested above, the assets can take the form of virtually any software component that the system designer desires to be able to validate. This can include components of user instructions or other information that may be utilized during emergency use of a defibrillator as described above; instructions or information useful in training, maintenance, monitoring or other non-emergency uses of the defibrillator; and/or any other desired types of information, commands or instructions. The assets can be graphic in nature suitable for display on a screen (e.g. one or more images, cine-loops, video segments and/or textual materials), audio assets suitable for playing through a speaker alone or in parallel with the display of graphics, code directing the control of various user interface components (e.g., controlling one or more indicator or warning lights on the defibrillator or on an external device) and/or a wide variety of other software components.

The audio and/or graphic assets can convey any desired type of information. For example, in some implementations they may include: spoken audio instructions or graphic instructions regarding how to use the AED during an emergency and/or appropriate steps to take when responding in an incident in which a victim may have suffered cardiac arrest; spoken and/or graphic instructions or information about the AED, cardiac arrest in general, AED training materials; information regarding the status or maintenance of the AED; etc. In another example, the assets may include executable code—as for example, code to activate a visual or audio indication or warning. For example, if the AED or an associated interface device has indicator lights to display the status of the AED, selected assets may include code that controls such lights (e.g., turning an indicator light on or off, blinking or flashing a light, directing the color of an indicator light (red, green, etc.)). In other embodiments, an asset can be used to generate an audio warning such as a chirp, beep, buzz or other sound clips to attract the attention of a user or individuals in the vicinity of the AED. In still other implementations, the asset can include code intended for controlling operation of the defibrillator itself or a component of the defibrillator or an external device that is associated with the defibrillator. Of course, the assets can be used for a wide variety of other purposes as well.

An asset header is associated with each asset and populated appropriately as represented by steps 406-423. Specifically, for each asset, an asset header is associated with the asset as represented by block 409. The asset header is then populated as represented by block 412. In implementations that utilize an asset header 360 having the structure illustrated in FIG. 1, the asset header may be populated by inserting the Asset Header Size indicator 363 in the Asset Header Size field 362; the Asset File Size indicator 366 in the Asset File Size field 365; the relative path and file name 375 in the Path field 374; and the Path Size indicator 372 in the Path Size field 371.

A hash function, which is preferably a cryptographic hash, is then performed on the asset to obtain an asset hash value 369 which is inserted into Asset Hash field 368 as represented by blocks 415 and 418. As discuss above, the hash of the asset can be performed on the asset body 380 alone or on a combination of the asset header 360 (or a portion thereof) and the asset body 380.

In some implementations, it will be desirable to encrypt the asset. When encryption is desired, the asset may be encrypted using any appropriate encryption algorithm as represented by optional block 420. At this stage, the asset is ready to be inserted into the container file 300 and is so inserted as represented by 422.

Once all of the assets have their associated headers and have been inserted into the container file as represented by the no branch of block 423, a container header 310 is associated with the container file as represented by block 424. The container header is then populated as represented by block 427. In implementations that utilize a container header 310 having the structure illustrated in FIG. 1, the container header may be populated by storing the appropriate values in the various fields of the container header 310. This may include storing an indication of the file format version utilized in to create the container header as File Format Version indicator 313 in the File Format Version field 312. Container Size indicator 316, which indicates the size of the container file is stored in the File Container Size Field 315. A count of the number of assets included in the container file is stored as the Number of Assets indicator 319 in the Number of Assets Field 318. The current date and time (which serves as Creation Time indicator 322) is stored in the Creation Time Field 321. A brief description of the contents of the file may be stored as file description 332 in the File Description Field 331. When used, a File Description Size indicator 328 may be stored in the File Description Size Field 327.

A hash function, which is preferably a cryptographic hash, is then performed on the container 300 itself to obtain a container hash 325 which as represented by block 430. The container hash 325 may then be inserted into File Hash Field 324 as represented by block 433. As discuss above, the hash of the container can be performed on the assets 350 alone or on a combination of the container header (or a portion thereof) and the assets 350.

In some implementations, it will be desirable to encrypt the container file. When encryption is desired, the container file may be encrypted using any suitable encryption scheme as represented by optional block 436. Neither asset encryption nor container file encryption is required. However in many implementations it will be desirable to encrypt the contents of the container file and either container level encryption or asset level encryption may be utilized for the purpose. If extremely strong encryption is desired, the contents can be encrypted at both the asset and container levels. In such arrangements, the encrypted assets are encrypted again as part of the container.

Once the container 300 has been fully populated including both the container header 310 and all of the assets, the container file is completed and may be distributed as appropriate.

In some embodiments, it may be desirable to encrypt the container file as a whole or to encrypt various assets individually. When encryption is desired, standard encryption techniques can be used to encrypt the container file and/or the assets. As with the hashes, the encryption can be performed on the entire container file or asset, or on only the body portions of the container file or asset.

Once the container header is fully populated (including the container hash) and any desired encryption has been performed the container file 300 is completed. Thereafter, the container file may be distributed using any suitable technique including: via electronic transmission over a communications network including the Internet, various WANs, LANs, VPNs and/or other networks; through downloads from an app store or other server; via physical media such as memory sticks, memory cards or other suitable computer readable memory devices; installed on a medical device for downloading onto cooperative devices; and/or any other suitable technique.

The described container file can be used to distribute software assets to a wide variety of different medical devices and/or devices that may be used in conjunction with medical devices. As suggested above, one particular application of interest relates to automated external defibrillators (AEDs). The applicant has described AEDs whose functionalities may be supplemented by an external device that is not a component of the AED itself (e.g., an independent defibrillator interface unit or a mobile communication device). In some specific implementations, the container file may be used to transmit various files to such an external device for use by a defibrillator support app installed on the external device. In some circumstances, the container file may include assets that are intended or suitable for use by the defibrillator support application in conjunction with the defibrillator during emergency use of the defibrillator. This may include graphic user instruction suitable for display on the interface unit or mobile communication device that supplement audio instructions provided by the AED itself. As previously discussed, the container file may additionally or alternatively include audio assets, executable code assets, and other types of assets. When present, executable code assets can be arranged to control indicator lights or any other component of the external device. Other executable code assets can be designed for delivery to the AED itself and control operations of the AED or components thereof.

When a device that will make use of one or more of the assets receives a container file, the device preferably validates the container. Thus, for example, when the container file is initially received by an application program (e.g., a defibrillator support application running on a mobile communication device or a defibrillator interface unit), the application will validate the container and all of its contents. This helps ensure that the received container file is uncorrupted and suitable for use by the application. In some embodiments, the container file is validated each time the application program is launched. This repeated validation helps ensure that (a) the container file remains uncorrupted; and (b) the container file is compatible with the then current (executing) version of the application program.

Figure 3:
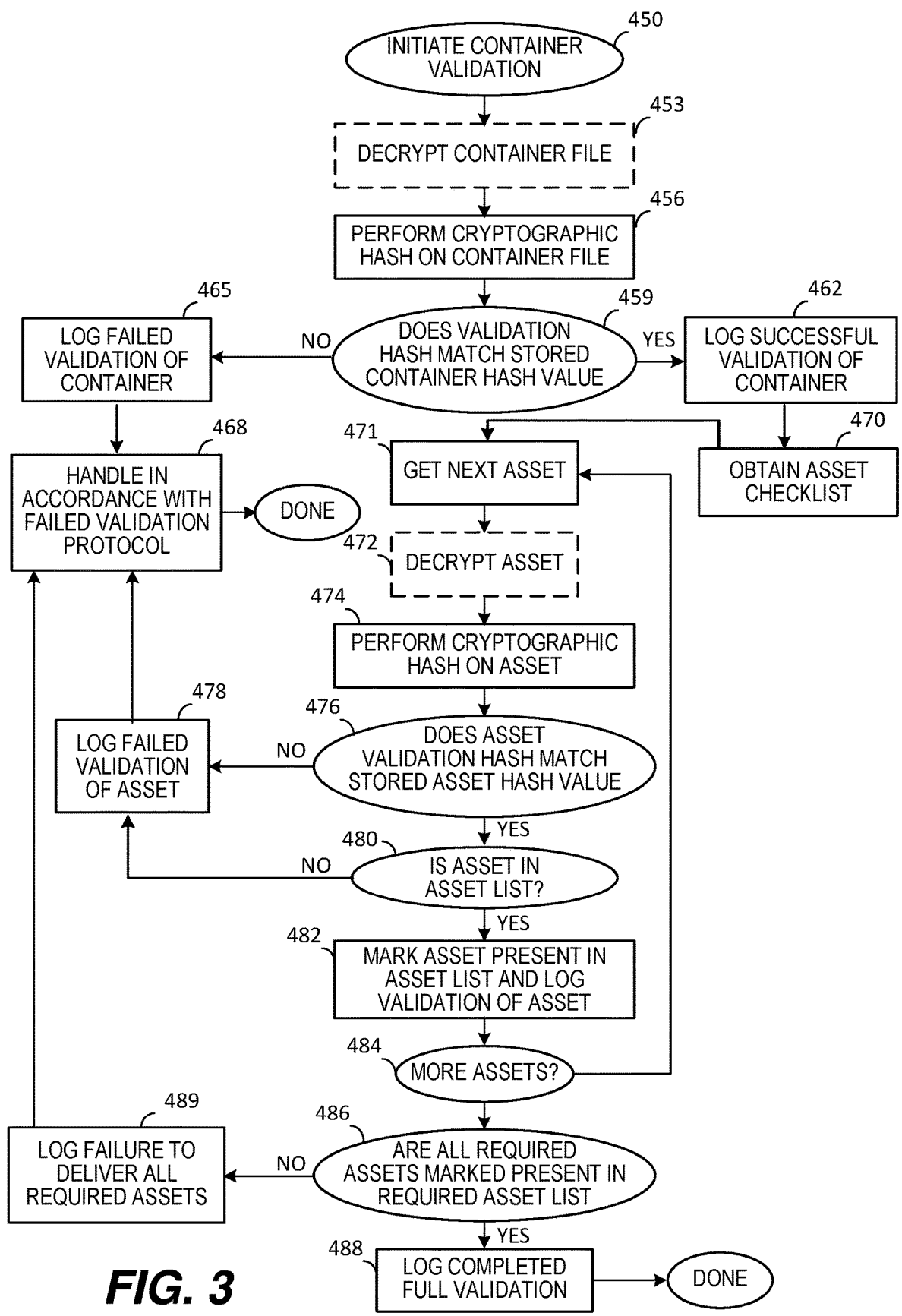
FIG. 3 is a flow chart illustrating a representative method of validating the container file of FIG. 1.

Referring next to FIG. 3, a validation scheme 350 in accordance with one embodiment will be described. The validation can be performed at any desired time including upon the initial receipt of the container file, upon the launching of an application program that may utilize one or more of the container assets, and/or at any other suitable time including upon receiving a request to use one of the assets in the container.

If the container file is received or stored in an encrypted format and the encryption was done after the container header is complete, the process may begin by decrypting the container file as represented by optional decryption block 453. In some implementations the decryption may be done when the container file is first received and the decrypted file may be persistently stored in decrypted form so that decryption is not required each time the application program is launched. In other implementations, the container file may be stored persistently in an encrypted form and decrypted each time that the application is launched or first uses the container file in a session or at other appropriate times.

After any required decryption is performed, a hash is performed on the container file to obtain a container validation hash as represented by block 456. The same hashing algorithm is used to generate the container validation hash as was used to generate the container hash value 325 stored in container header 310. As indicated above, the hashing algorithm is preferably (but not necessarily) a cryptographic hashing algorithm. The resulting container validation hash is then compared to the container hash value 325. If the hashes match, the container level validation was successful. Alternatively, if the container validation hash does not match the stored container hash value 325, then the container file is deemed corrupted. Any failure of the validation is preferably logged as represented by block 465 and the container file is treated as corrupted and situation is handled in accordance with a failed validation protocol as represented by block 468. If the container is successfully validated via a determination that the hash values match, the occurrence of a successful validation of the container is preferably logged as represented by block 462. There are a number of benefits to logging, some of which will be discussed in more detail below.

Once the container has been validated a process is undertaken to validate each of the assets held in the container file, preferably on an individual basis as will be discussed with references to elements 470-484 of the flow chart of FIG. 3.

In some embodiments, each application program that is designed to utilize the container file contains an asset list that identifies all of the components that the application program expects to be included in the container file. That is, the application program knows the assets it expects to receive as part of the container file. This provides an additional level of security because it allows the application to verify that each of the expected assets is actually present. If the container file does not include all of the expected assets, a fault (failed validation) may be identified.

In the illustrated embodiment, the validating program contains a required assets checklist (not shown) that identifies the path and file name for all of the expected assets and provides a mechanism for individually marking the presence of each asset. The marker for each asset may be a simple "present" flag or any other suitable data structure suitable for marking the presence of the individual assets. The validating program conceptually obtains the required assets checklist as represented by block 470. In practice, this may be accomplished by initializing a required asset checklist data structure or clearing the required asset checklist data structure so that none of the assets are marked as present.

The assets are then individually verified which begins by obtaining the first (next) asset as represented by block 471. If the assets are encrypted, the first (next) asset is decrypted as represented by the optional asset decryption block 472. If the asset is not encrypted, the decryption step may be skipped. A hash is then performed on the selected asset to obtain an asset validation hash as represented by block 474. The same hashing algorithm is used to generate the asset validation hash as was used to generate the asset hash value 369 stored in asset header 360. As indicated above, the hashing algorithm is preferably (but not necessarily) a cryptographic hashing algorithm. The resulting asset validation hash is then compared to the asset hash value 369 as represented by block 476. If the hashes match, the asset level validation of the selected asset was successful. Alternatively, if the asset validation hash does not match the stored asset hash value 369, then the asset is deemed corrupted. Any failure of the validation is preferably logged as represented by block 478 and the asset is treated as corrupted and situation is handled in accordance with the failed validation protocol as represented by block 468.

The relative path and file name are also verified by checking the required assets checklist. Since the asset checklist includes the path and filename for each of the expected assets, the relative path and file name may be verified by checking to see whether the asset is identified in the asset list as represented by decision block 480. If the asset is found in the asset list, the asset is marked as present in the asset list and the successful validation of the asset is preferably logged as represented by block 482. If not, the asset validation fails and the failure is preferably logged as represented by block 478.

After an asset has been verified, the logic moves to the next asset as represented by decision block 484. If there are more assets, the next asset is validated using the same process as described above (steps 471-484). Once all of the assets have been validated, a check is performed to make sure that all of the assets are marked as present in the required assets checklist as represented by block 486. If all of the required assets are present in the container file, then the container file has been fully validated (including all of the assets) and the successful validation is logged as represented by block 488 and the validation is completed.

As suggested above, the validation can be performed at any desired time including upon the initial receipt of the container file and each time that an application program that may utilize one or more of the container assets is launched. This repeated validation has several advantages. It ensures that both (a) the container file is verifiably uncorrupted, and (b) that the container file is the appropriate version for the application program. Thus, for example, if either the container file or the application file is outdated, such that the versions are inconsistent for any reason, that inconsistency can be detected and resolved at an early stage. Logging the results of the validation gives a clear record that can be used to verify and show that the appropriate software is being used in conjunction with the medical device when the two are used in combination. Aggressively logging intermediate results such as the initial container hash check, each of the asset validations, and the asset list check can also be useful in determining exactly what went wrong in the event that a validation fails. This can be useful in determining what steps are appropriate to rectify the issue. The appropriate response (block 468) will often depend on the nature of the fault. For example, if it is determined that the application program is out of date because the container file is a more recent version than can be handled by the application program, the appropriate handing may include prompting the user to update the application program (e.g., by downloading the most recent version from an app store or other appropriate server) or an automatic download may be initiated. Conversely, if the container file is out of date because the application program is a more recent version than the container file, an updated container file may be automatically requested or the user may be prompted to do the same. If there is a problem with the version of the application program or the container file that is being used, the application program may optionally be disabled so that it cannot be used in conjunction with the medical device unless or until it is updated and the problem fixed.

Figure 4:
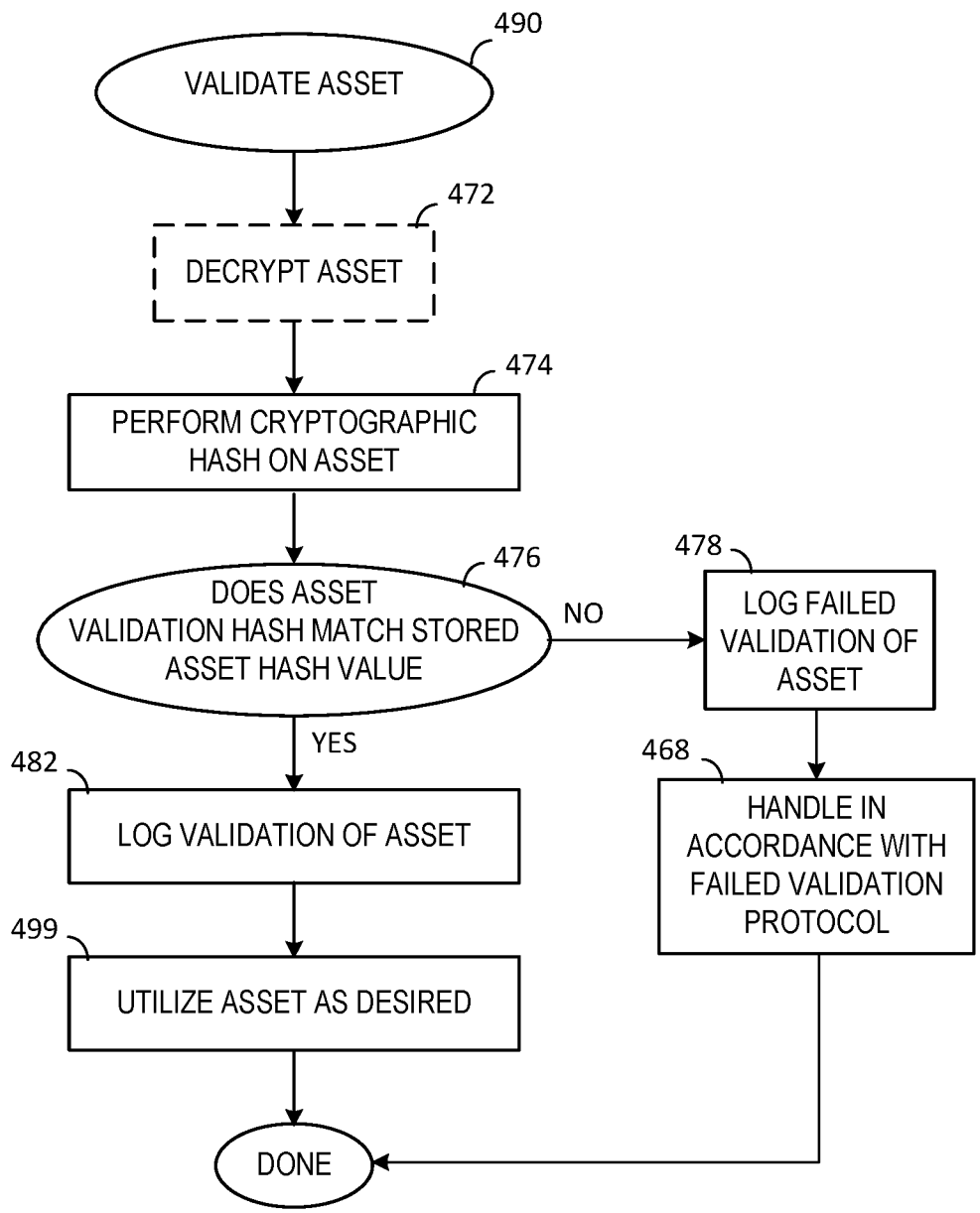
FIG. 4 is a flow chart illustrating a representative method of validating an asset.

In some circumstances, it may also be desirable to validate an asset each time that the asset is actually used. This can be useful even when the container file including all of the assets have been validated when the application program was launched. Such an approach can help mitigate any risk that the asset may have been corrupted after the initial validation but before the asset is actually used. FIG. 4 is a flow chart that illustrates a use time asset validation approach. This use time asset validation 490 may be quite similar to the asset validation utilized in the container validation described above.

If the assets are stored at runtime in an encrypted format, the asset is decrypted as represented by the optional asset decryption block 472. If the asset is not encrypted, the decryption step may be skipped. A hash is then performed on the selected asset to obtain an asset validation hash as represented by block 474. The same hashing algorithm (which may be cryptographic) is used to generate the asset validation hash as was used to generate the asset hash value 369 stored in asset header 360. The resulting asset validation hash is then compared to the asset hash value 369 as represented by block 476. If the hashes match, the asset validation was successful, the successful validation is logged (block 482) and the asset may be utilized as desired as represented by block 499. Alternatively, if the asset validation hash does not match the stored asset hash value 369, then the asset is deemed corrupted. Any failure of the validation is preferably logged as represented by block 478 and the asset is treated as corrupted and situation is handled in accordance with the failed validation protocol as represented by block 468.

The specific actions that are taken in response to a failed asset validation may vary widely based on the needs of any particular situation. In some implementations, the asset is deemed invalid and a message is displayed or otherwise rendered instructing the user to follow the instructions provided by the medical device itself. For example, in the context of a defibrillator support application, the AED may be configured to provide audio instructions that are supplemented by the synchronous display of corresponding graphic and/or textual instructions on the display of a mobile communication device or interface device running the defibrillator support application. In such circumstances, if an asset validation fails during emergency user on an AED, it may be desirable to terminate the display of synchronized graphic instructions and post a message that informs the user to follow the audio instructions provided by the AED itself.

The described container file can be used to distribute software components to a wide variety of different medical devices and/or devices that may be used in conjunction with medical devices. As suggested above, one particular application of interest relates to automated external defibrillators (AEDs). The applicant has described AEDs whose functionalities may be supplemented by an external device that is not a component of the AED itself (e.g., an independent defibrillator interface unit or a mobile communication device). In some specific implementations, the container file may be used to transmit various files to such an external device for use by a defibrillator support app installed on the external device. In some circumstances, the container file may include assets that are intended or suitable for use by the defibrillator support application in conjunction with the defibrillator during emergency use of the defibrillator. This may include graphic user instruction suitable for display on the interface unit or mobile communication device that supplement audio instructions provided by the AED itself.

Representative Defibrillator Architecture

Figure 5A:
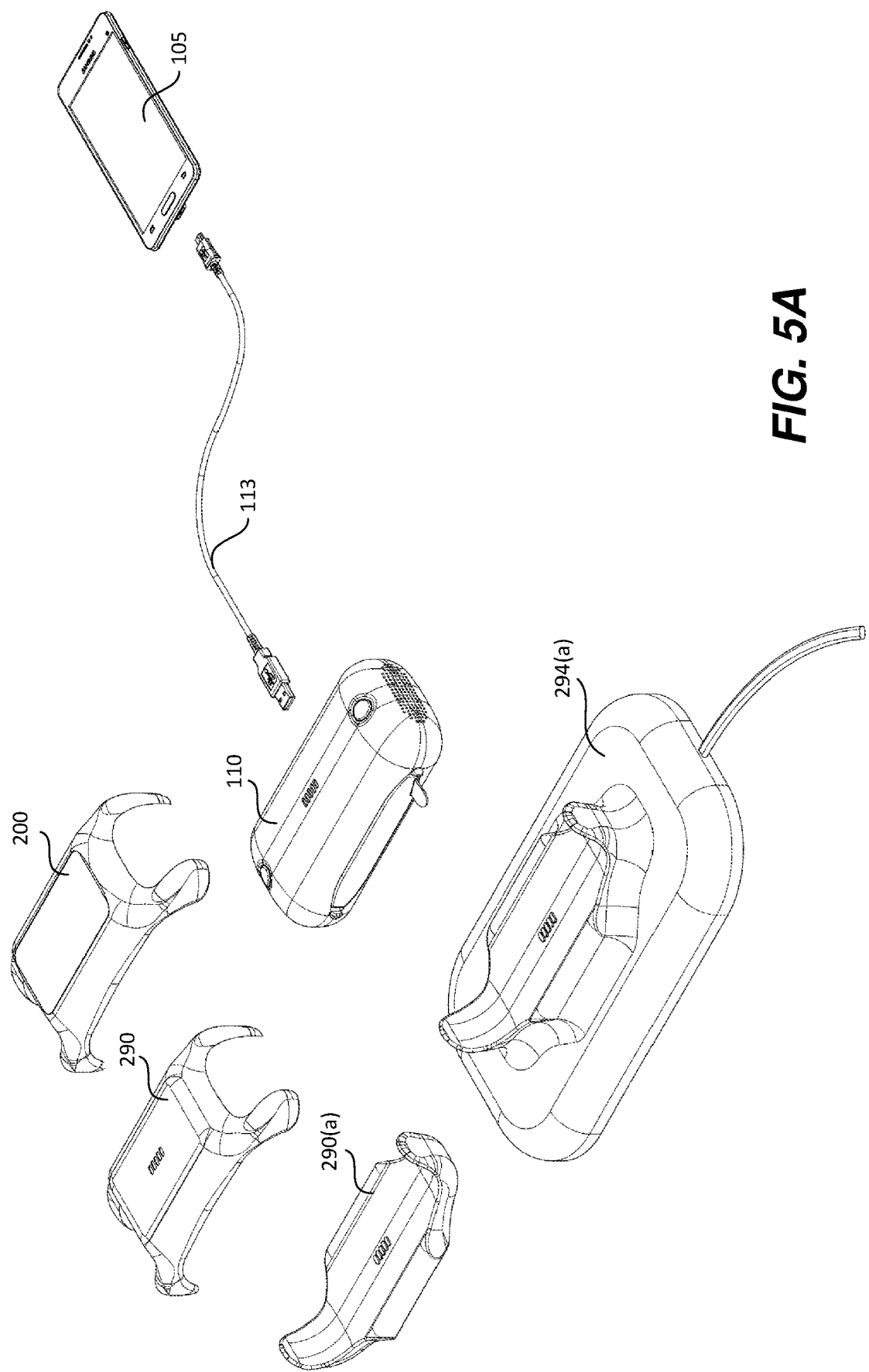
FIGS. 5A-5C are diagrammatic illustrations of components of a representative automated external defibrillator together with selected external devices that may benefit by using the described frameworks, methods and container structures.
Figure 5B:
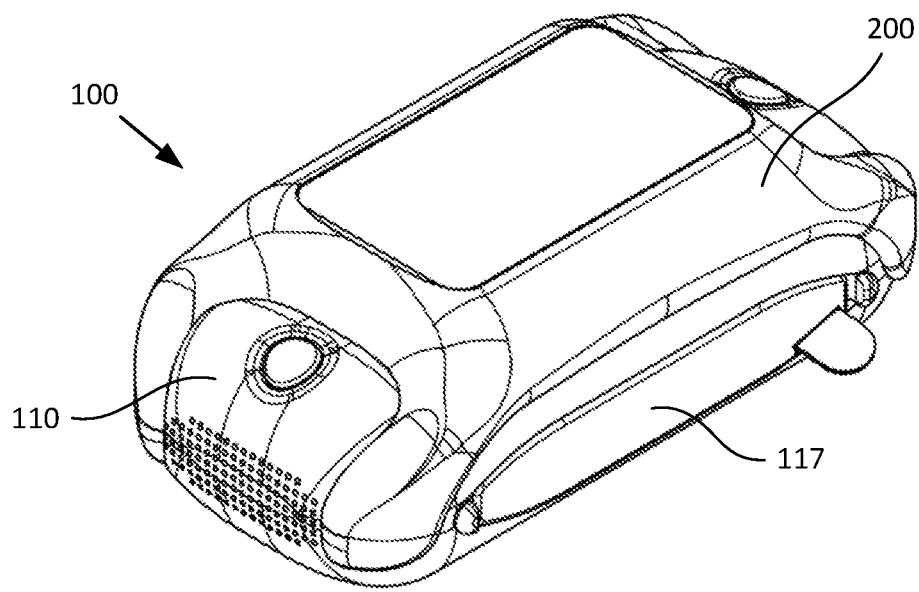
Figure 5C:
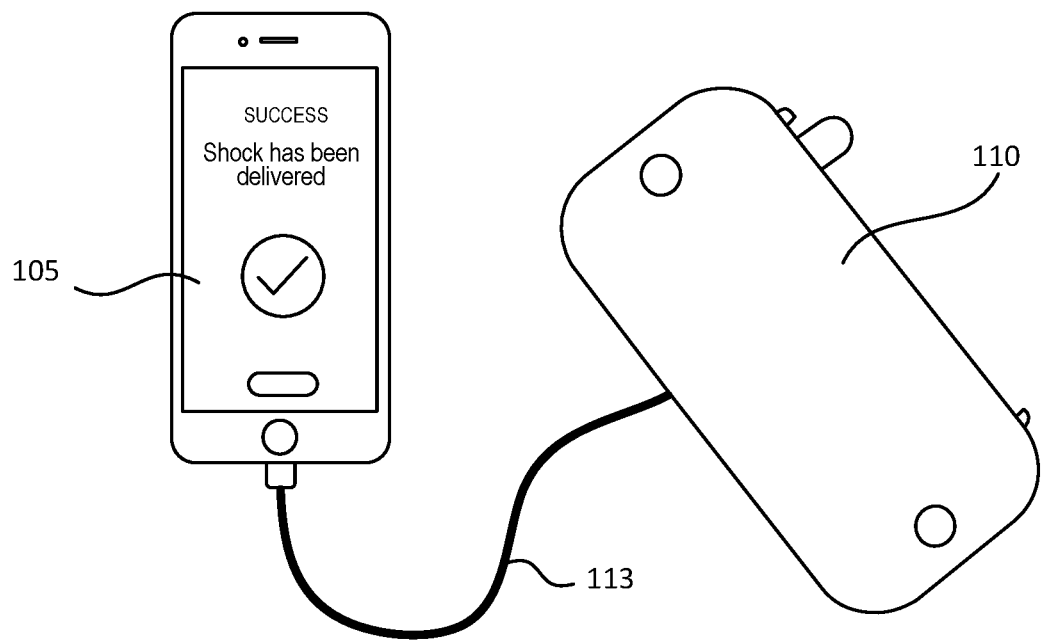

Referring next to FIGS. 5A-5C, a modular defibrillator architecture that can benefit from the described framework in accordance with one embodiment will be described. The illustrated architecture is well suited for use in automated external defibrillators (including both semi-automated and fully automated defibrillators) although it may also be used in manual defibrillators and hybrid defibrillators that may be used in either automated or manual modes.

The core of the modular defibrillator system 100 is a base defibrillation unit (base unit) 110. The base defibrillation unit 110 is a fully functional defibrillator that is configured so that its functionality can be supplemented by connecting the base unit 110 to a mobile communication device 105 (such as a smartphone, a tablet computer, etc.) having a defibrillator control app installed thereon, or by attaching an interface unit 200 to the base unit 110.

The interface unit 200 is ideal for enterprise applications as it may have wireless communication capabilities (e.g., Cellular, Wi-Fi, Bluetooth, etc.) and/or position sensing capabilities (e.g., GPS, GNSS, etc.) to improve both: (a) in-emergency patient care; and (b) unit tracking, maintenance and updating. In some embodiments, the interface unit also has a display screen that can be used to display graphics and/or videos that can assist in both emergency and maintenance & monitoring activities. For users that do not require an interface module that permanently connects to the base unit, the wireless connectivity, as well as graphical touch screen functionality, can be made available by connecting a personal communication device such as a smartphone or tablet computer with a defibrillator app installed thereon to the base unit. Both the interface unit and a connected personal device executing a defibrillator app can be configured to facilitate training, which can take a wide variety of forms—as for example by: displaying training videos; providing answers to frequently asked questions (FAQs); accessing external resources; and providing guidance through visual cues during an emergency, such as how to perform CPR or where to place the electrode pads.

In FIG. 5A, the base unit 110, the mobile communication device 105 and the interface unit 200 are shown separately to highlight those separate components. In FIG. 5B, the interface unit 200 is shown attached to the base unit 110 illustrating one particular use scenario in which the interface unit is used as a supplemental interface for the base defibrillator unit. In FIG. 5C, a mobile communication device 105 is shown attached to the base unit 110 illustrating a second use scenario in which the mobile communication device 105 is utilized as a supplemental interface and power supply for the base defibrillator unit.

When an interface unit 200 or a mobile communications device 105 with a defibrillator support App installed thereon are connected with the base defibrillator unit 110 during an emergency, the connected device can be arranged to display graphic instructions to a user that match the instructions issued from the base unit (e.g. an audio instruction issued by the base unit, although the base unit may issue instructions in other formats as well). As the base unit gives different instructions to the user, the graphic instructions displayed on the mobile communications device or interface unit change to match the instructions from the base unit.

The synchronization between the base unit and a connected interface unit or mobile communication device can be accomplished using a variety of different approaches. By way of example, the base unit may be configured to periodically send status messages to any display device that is connected to the base unit (e.g., an interface unit 200 and/or a connected mobile device 105). A couple such approaches are described in U.S. application Ser. No. 16/145,657 and 62/787,872, each of which is incorporated herein by reference.

The defibrillator support app 270 may use components from the container file 300 to generate the synchronized graphic instructions—which may take the form of one or more of images, text, graphics, cine-loops, video segments, animations, pictures, etc.

Figure 6:
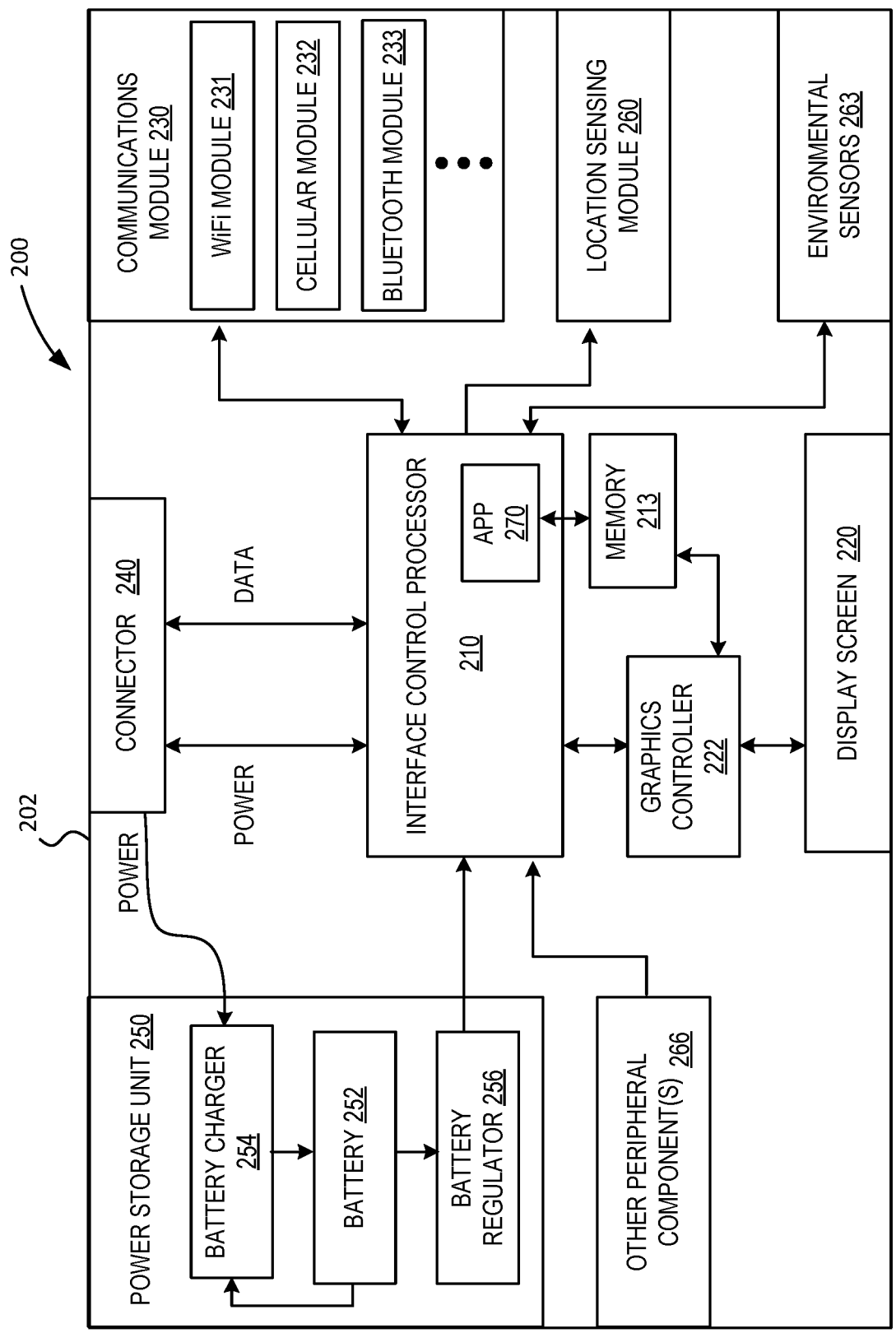
FIG. 6 is a diagrammatic illustration the architecture of an interface device suitable for use in the system illustrated in FIG. 5A.

FIG. 6 illustrates some of the electrical components of a particular interface unit 200 suitable for utilizing the described container files 300. In the illustrated embodiment, the interface unit 200 includes an interface controller (processor) 210, memory 213, a display screen 220, a communications module 230, an electrical connector 240, an interface unit power storage unit 250, and a location sensing module 260, all of which may be housed within the interface unit housing 202. The interface unit may also have software or firmware (such as a defibrillator support app 270) installed or installable in memory 213 having programmed instructions suitable for controlling operation of the interface unit, coordinating communications between the interface unit 200 and the base defibrillation unit 110 and/or remote devices and controlling the display 220. The memory 213 may take any suitable form of memory suitable for storing computer (processor) readable programmed instructions.

The processor 210 controls operation of the interface unit and coordinates communications with both the base unit 110 and remote devices such as a central server. In some embodiments, the processor 210 is arranged to execute a defibrillator app 270 that can be used both during use of the defibrillator system 100 during a cardiac arrest incident and to facilitate non-emergency monitoring or/and use of the defibrillator system 100. The defibrillator support app may also have programmed instructions suitable for validating the container file 300 as well as its assets 350 and for utilizing assets from the container file during emergency and/or non-emergency use of the AED.

The display screen 220 is suitable for displaying text, graphics and/or video under the direction of the processor 210 to assist both during both emergency situations and at other times. In some embodiments display screen 220 is touch sensitive screen suitable for receiving inputs based on a graphical user interface displayed thereon. In some embodiments an optional graphics controller 222 may be provided to facilitate communications between the interface control processor 210 and the display screen 220. When a graphics controller is provided, the graphics controller may alternatively or additionally include programmed instructions for utilizing assets from the container file.

The communication module 230 is provided to facilitate communications with remotely located devices such as the central server. The communications module 230 may be configured to utilize any suitable communications technology or combination of communication technologies including one or more of cellular communications, Wi-Fi, satellite communications, Bluetooth, NFC (Near Field Communications), Zigbee communications, DSRC (Dedicated Short Range Communications) or any other now existing or later developed communications channels using any suitable communication protocol. By way of example, in the illustrated embodiment, the communications module 230 includes Wi-Fi, cellular and Bluetooth modules 231, 232 and 232 that facilitate Wi-Fi, cellular and Bluetooth communications respectively.

The electrical connector 240 is configured to mate with interface connector 190 on the base defibrillator unit 110. The connectors 190 and 240 are configured to facilitate communications between the defibrillator controller 130 and the interface unit's processor 210. The connectors 190 and 240 are also preferably arranged to supply power from the interface unit 200 to the base unit 110 as will be described in more detail below. In some embodiments, power will only be provided in one direction—i.e., from the interface unit 200 to the base unit 110 and not in the reverse direction during operation. A good reason for this approach is that the defibrillator is the most important component from a safety standpoint and it is often undesirable to draw power from the base unit to power other devices (including the interface unit 200) in a manner that could reduce the energy available to charge the discharge capacitor in the event of an emergency.

The connectors 190 and 240 can take a variety of forms. They can be connectors with accompanying transceivers configured to handle processor level communications (such as UART, SPI, or I2C transceivers), with additional pins for power delivery (Power+GND), and connection verification (i.e. a pin that detects when there is a connection between the interface unit and the Base AED and triggers an interrupt on the Base AED signifying that there is not a unit connected). They can also be more standardized connectors such as USB connectors.

The interface power storage unit 250 provides power to operate the interface unit 210. In many embodiments, the power storage unit takes the form of a battery 252 with associated control components, although a variety of other power storage technologies such as supercapacitors, ultracapacitors, etc. may be used in other embodiments. The associated control components may include components such as a battery charger and maintainer 254, which may include various safety monitors, and battery regulator 256. Preferably, the power storage unit 250 is rechargeable, although that is not a requirement. In some embodiments it may be desirable to utilize replaceable batteries (rechargeable or not) so that the batteries in the power storage unit 250 can be replaced when they near the end of their useful life. In some embodiments, the power storage unit 250 may also be arranged to supply supplemental power to the base unit 110. Depending on the structure and/or state of the base unit, the supplemental power can be used to help charge the discharge capacitor 150 during use; to power or provide supplemental power for the defibrillator electronics and/or to charge the base defibrillator unit's power storage unit. In other embodiments, a supplemental battery within the interface unit (not shown) may be used to provide the supplemental power for the base unit rather than the power storage unit 250.

The interface unit may also optionally include various environmental sensors 263 and other peripheral components 266. When desired, the interface unit may include any of a wide variety of different types of sensors and peripheral components. For example, in selected embodiments, the interface unit may include one or more accelerometers and/or gyroscopes, a temperature sensor, a humidity sensor, a time of day or any other desired sensors or components.

The interface unit 200 is preferably configured to securely mechanically attach to the base unit 110. Typically, the interface unit is detachable such that it may be separated from the base unit if desired—although in other embodiments, the attachment may be more permanent in nature. The specific mechanical attachment utilized may vary widely in accordance with the needs of any particular embodiment. In some embodiments, press or form fitting attachment structures are used, while in others, latch and catch mechanisms, snap fit structures, etc. are utilized alone or in combination to releasably attach the interface unit to the base. However, it should be appreciated that a wide variety of other structures can be used in other embodiments. In some embodiments, the interface unit includes an attachment sensor (not shown) that senses when the interface unit is attached to a base unit.

Although specific defibrillator and interface unit structures have been shown for illustrative purposes, it should be appreciated that the described container based software component approach can be used in conjunction with virtually any defibrillator (or other medical device) that has the capacity to receive and process the container files. It can also be used with virtually any external device that is configured to cooperatively work with a defibrillator (or other medical device) so long as the external device has the capacity to receive and process container files.

The base unit 110 can also be coupled to a mobile communication device 105 such as a cell phone, a tablet computer, a personal digital assistant (PDA) or other portable computing device as seen in FIG. 1C. In the embodiment illustrated in FIG. 1C, the mobile communication device takes the form of a smartphone such as a Samsung Galaxy or an Apple iPhone. However, in other embodiments, a wide variety of other cell phones or other mobile communication devices may be used in place of the smartphone. The internal structure of the mobile communication device is not explicitly shown because the structure of such devices are well known, although they may vary widely.

Such devices typically have the processors, memory, communication capabilities suitable for receiving, storing and processing the container file under the direction of a suitable app or other suitable software component.

The mobile communication device 105 is coupled to the base defibrillation unit 110 via a connector cable 113 that plugs into the connector port. In other embodiments, the connector port can be replaced by a connector cable that is permanently hard wired to the defibrillation unit. In still other embodiments, the mobile communication device can couple wirelessly with the base unit.

A defibrillator app 270 can be installed on the mobile communication device 105 to provide much or all of the defibrillator interface, control, monitoring and reporting functionality available to the defibrillator. The mobile communication device 105 can also provide power to the base defibrillation unit 110. In some preferred embodiments, power drawn from the mobile communication device is sufficient to power all of the base unit's electronics, including charging the discharge capacitor to a level suitable for shock delivery in a timely manner to facilitate use of the base unit even in the circumstance that the base unit's power storage unit is completely drained and no other power is available to the base unit. That is, if necessary, the base unit 110 can be operated in a mode analogous to the arrangement described in Applicant's U.S. Pat. No. 10,029,109 which is incorporated herein by reference.

As suggested above, the attachment of the interface unit 200 or the connection of a personal phone or other mobile communication device 105 that has a defibrillator app installed thereon supplements the functionality of the base unit in a number of ways. For example, during emergency use, the system can automatically call 9-1-1, report the location of the victim and open a line of communication between Emergency Medical Services (EMS) and lay on-scene users. This fits nicely with the U.S. federal initiative to expand emergency communications to include wireless and voice-over-IP devices (Next-Generation 9-1-1), text and video messaging, and geolocation. The container file 300 may contain assets that facilitate or assist with such communications.

Further, critical incident related information such as the time since first shock, type of arrhythmia detected, number of shocks delivered, etc., can be relayed to responding EMS personnel en route, as well as displayed on the interface unit or personal phone screen once the emergency personnel arrive. Such real-time communication speeds patient transitions between responders and decreases communication errors, ultimately improving patient outcomes. The container file 300 may also contain assets that facilitate or assist with such communications.

Outside of an emergency, the described system can automate the maintenance process. For entities with several AED units, the GPS location of each unit, expiration dates, battery level, versions, etc. can all be accessed on a backend management platform. For all users, any critical notifications, including battery low, device expirations, and system self-test failure indicating a problem with the AED unit, can be automatically sent via email and SMS to the appropriate personnel. Instead of AED fleet managers needing to manually inspect each AED monthly, the information is available at their fingertips. This can go a long way in addressing the current issue of ensuring AEDs are properly maintained. The container file 300 may contain assets that facilitate or assist with such notifications.

The attachment of an interface unit 200 or the connection of a mobile communication device 105 to the base unit also provides a mechanism for facilitating software updates to the base unit itself. Specifically, secure software updates can be received by the interface unit or mobile communication and then transferred to and installed on the base unit 110. This type of remote software updates allow for device performance improvements, as well as critical fixes for any bugs that arise without needing to physically retrieve each unit. The ability to update any encountered bug helps ensure that the AED is ready to go when needed. Again, the container file 300 may contain assets that facilitate such software updates.

In some embodiments, the interface unit has no substantial function other than to operate in conjunction with the defibrillator but is not required for the defibrillator to operate properly. Indeed, in some embodiments, the interface unit cannot function when it is not connected to a defibrillator.

Although only a few embodiments of the invention have been described in detail, it should be appreciated that the invention may be implemented in many other forms without departing from the spirit or scope of the invention. The described methods, frameworks and container structures provided mechanisms for validating software components (assets) to help ensure that they are valid and uncorrupted when they are used. Such validation can be particularly important when unregulated (or less regulated) devices such as smartphones, tablet computers and other mobile communication devices or other personal computing devices that cannot be or are not controlled by a medical device manufacturer are used in conjunction with medical devices or enhance the user's experience when operating the medical device.

The inventions have been described primarily in the context of use scenarios involving software components installed on devices used in conjunction with defibrillators. However, it should be appreciate that the described approach can be used in conjunction with a wide variety of other medical device and/or medical information management applications as well. Still further, the described methods, frameworks and container structures are well suited for validating software components installed directly on a medical device (including defibrillators). Therefore, the present embodiments should be considered illustrative and not restrictive and the invention is not to be limited to the details given herein, but may be modified within the scope and equivalents of the appended claims.

What is claimed is:

1. A method for validating a container file for use by a defibrillator support application configured for use in conjunction with a defibrillator, the defibrillator support application having a required assets list, the container file including a container header and a plurality of assets suitable for use by the defibrillator support application, each asset including asset data and an asset header appended to the asset data, the method comprising:

hashing at least a portion of the container file using a first hashing protocol to create a first hash value, wherein the hashed portion of the container file includes at least all of the asset data of all of the assets;

comparing the first hash value to a container file hash stored in the container header to determine whether the first hash value matches the container file hash, wherein when the first hash value and the container file hash do not match, the container file is treated as not valid;

for each asset included in the container file, (i) hashing at least a portion of the asset using a second hashing protocol to create an asset validation hash value, wherein the hashed portion of the asset includes at least the asset data associated with the asset, and (ii) comparing the asset validation hash value to an original asset hash value stored in the asset header associated with the asset to determine whether the asset validation hash value matches the original asset hash value, wherein when the asset validation hash value and the original asset hash value do not match, the container file is treated as not valid;

verifying that all assets identified in the required assets list are present in the container file, wherein when one or more assets identified in the required assets list are not present in the container file, the container file is treated as not valid; and wherein the container file is only validated when at least the first hash value matches the container file hash value, each asset validation hash value matches the associated original asset hash value, and all of the assets identified in the required assets list are present in the container file.

2. A method as recited in claim 1 wherein the defibrillator support application is installed and executes on an external device that is separate from the defibrillator, the external device including a display screen, the method further comprising displaying user instructions for the defibrillator on the external device using one or more of the assets from the validated container file.

3. A method as recited in claim 1 wherein the defibrillator support application is installed and executes on an external device that is separate from the defibrillator, the external device including a display screen, the method further comprising causing a message to be displayed on the display screen informing a user to follow instructions from the defibrillator when the container file is not valid.

4. A method as recited in claim 1 wherein the method is performed by the defibrillator support application:
when the container file is initially received by the defibrillator support application; and
each time the defibrillator support application is launched.

5. A method as recited in claim 1 further comprising, in response to a request from the defibrillator support application to access a selected one of the assets during emergency use of the defibrillator:
hashing at least a portion of the asset using the second hashing protocol to create an accessed asset hash value, wherein the hashed portion of the selected asset includes at least the asset data associated with the selected asset; and
comparing the accessed asset hash value to the original asset hash value stored in the asset header associated with the selected asset, wherein the defibrillator support application is only able to utilize the selected asset when it is determined that the accessed asset hash value and the original asset hash value match.

6. A method as recited in claim 1 wherein each asset header includes:
an asset file size field having a file size indicator that indicates a size of the associated asset;
an asset hash field that includes the asset hash that is a hash of at least the asset data for the associated asset; and
a path field that identifies at least a portion of a path suitable for accessing the asset.

7. A method as recited in claim 1 wherein the container header includes:
a container size field that includes a container size indictor that indicates a size of the container; and
a container file hash field that includes the container file hash that is a hash of at least the plurality of assets including the asset header and asset data associated with each asset.

8. A method as recited in claim 7 wherein the container header further includes at least one of:
a file format version field that includes a file format version indicator;
a number of assets field having a number of assets identifier that indicates a number of assets contained in the container; and
a creation time field that indicates when the container was created.

9. A method for validating of a container file for use by a medical device support application configured for use in conjunction with a medical device, the container file including a container header and a plurality of assets suitable for use by the medical device support application, each asset including an asset header and asset data, wherein each asset header includes (i) an asset file size field having a file size indicator that indicates a size of the associated asset, (ii) an asset hash field that includes an asset hash that is a hash of at least the asset data for the associated asset, and (iii) a path field that identifies at least a portion of a path suitable for accessing the asset, the method comprising:
hashing at least a portion of the container file using a first hashing protocol to create a first hash value, wherein the hashed portion of the container file includes at least all of the asset data;
comparing the first hash value to a container file hash stored in the container header to determine whether the first hash value matches the container file hash, wherein when the first hash value and the container file hash do not match, the container file is treated as not valid;
for each asset included in the container file, (i) hashing at least a portion of the asset using a second hashing protocol to create an asset validation hash value, wherein the hashed portion of the asset includes at least the asset data associated with the asset, and (ii) comparing the received asset validation hash value to an original asset hash value stored in the asset header associated with the asset to determine whether the asset validation hash value matches the original asset hash value, wherein when the asset validation hash value and the original asset hash value do not match, the container file is treated as not valid; and
wherein the container file is only validated when at least the first hash value matches the container file hash value and each asset validation hash value matches the associated original asset hash value.

10. A method as recited in claim 9 wherein the medical device support application includes a required assets list, the method further comprising verifying that all assets identified in the required assets list are present in the container file, wherein when one or more assets identified in the required assets list are not present in the container file, the container file is treated as not valid.

11. A method as recited in claim 9 wherein the method is performed by the medical device support application when the container file is initially received by the medical device support application, the method further comprising storing the validated container file in memory for use by the medical device support application.

12. A method as recited in claim 9 wherein the method is performed by the medical device support application each time the medical device support application is launched.

13. A method as recited in claim 9 further comprising, in response to a request from the medical device support application to access a selected one of the assets during emergency use of the medical device:
   hashing at least a portion of the selected asset using the second hashing protocol to create an accessed asset hash value, wherein the hashed portion of the selected asset includes at least the asset data associated with the selected asset; and
   comparing the accessed asset hash value to the original asset hash value stored in the asset header associated with the selected asset, wherein the defibrillator support application is only able to utilize the selected asset when it is determined that the accessed asset hash value and the original asset hash value match.

14. A method as recited in claim 9 wherein the first and second hashing protocols are cryptographic hashing protocols.

15. A method as recited in claim 9 wherein the first and second hashing protocols are the same hashing protocol.

16. A method as recited in claim 9 wherein the medical device support application is installed and executes on an external device that is separate from the medical device, the external device including a display screen, the method further comprising displaying user instructions for the medical device on the external device using one or more of the assets from the validated container file.

17. A method as recited in claim 9 further comprising displaying medical device user instructions.

18. A method as recited in claim 9 further comprising creating the container file by:
   for each of the plurality of assets, hashing at least the body portion of the asset to create the original asset hash value and inserting the original asset hash value into an asset hash field in the asset header;
   inserting each of the assets into the container file;
   hashing at least a portion of container file including at least all of the assets to create the container hash; and
   inserting the container hash into a container hash field in the container file.

19. A method for validating a container file for use by a medical device support application configured for use in conjunction with a medical device, the container file including a container header and a plurality of assets suitable for use by the medical device support application, each asset including an asset header and asset data, the method comprising:
   hashing at least a portion of the container file using a first hashing protocol to create a first hash value, wherein the hashed portion of the container file includes at least all of the assets;
   comparing the first hash value to a container file hash stored in the container header to determine whether the first hash value matches the container file hash, wherein when the first hash value and the container file hash do not match, the container file is treated as not valid; and
   for each asset included in the container file, (i) hashing at least a portion of the asset using a second hashing protocol to create an asset validation hash value, wherein the hashed portion of the asset includes at least the asset data associated with the asset, and (ii) comparing the received asset validation hash value to an original asset hash value stored in the asset header associated with the asset to determine whether the asset validation hash value matches the original asset hash value, wherein when the asset validation hash value and the original asset hash value do not match, the container file is treated as not valid; and
   wherein the container file is only validated when at least the first hash value matches the container file hash value and each asset validation hash value matches the associated original asset hash value;
   wherein each asset header includes (i) an asset file size field having a file size indicator that indicates a size of the associated asset, (ii) an asset hash field that includes the asset hash that is a hash of at least the asset data for the associated asset, and (iii) a path field that identifies at least a portion of a path suitable for accessing the asset; and
   wherein the container header includes (i) a file format version field that includes a file format version indicator, (ii) a container size field that includes a container size indictor that indicates a size of the container, and (iii) a container file hash field that includes the container file hash that is a hash of at least the plurality of assets including the asset header and asset data associated with each asset.

20. A method as recited in claim 19 wherein the assets contained in the asset file include a multiplicity of components for use in instructions generated by the medical device support application to help guide an operator's use of the medical device.

21. A method as recited in claim 19 wherein the asset hashes and the container file hashes are cryptographic hashes.

22. A method as recited in claim 21 wherein the container file hash is a hash of at least the container header and the plurality of assets including the asset header and asset data associated with each asset.

23. A method as recited in claim 19 wherein the path is a relative path.

24. A method as recited in claim 19 wherein each asset header further includes:
   an asset header size field having an asset header size indicator that indicates a size of the asset header; and
   a path size field that includes a path size indicator that indicates a size of the path field.

25. A method as recited in claim 19 further wherein the container header further includes:
   a number of assets field that includes a number of assets identifier that indicates the number of assets contained in the container file;
   a creation time field that includes a creation time indicator that identifies a file creation date and time;
   a file description field that includes a description of the file; and
   a file description size indicator that indicates a size of the description of the file.

* * * * *